United States Patent

Aoyagi et al.

[11] Patent Number: 4,978,770
[45] Date of Patent: Dec. 18, 1990

[54] QUATERNARY AMMONIUM SALTS OF DICYANO SUBSTITUTED TERIARY ALKYLENE DIAMINES AS BLEACH ACTIVATORS

[75] Inventors: Muneo Aoyagi; Kazuhiro Takanashi; Masaaki Yamamura, all of Utsunomiya; Moriyasu Murata, Chiba; Hiroyuki Yamada, Tochigi; Hiroyuki Araki, Tochigi; Takanori Fukumoto, Tochigi, all of Japan

[73] Assignee: Kao Corporation, Tokyo, Japan

[21] Appl. No.: 502,335

[22] Filed: Mar. 30, 1990

Related U.S. Application Data

[62] Division of Ser. No. 229,913, Aug. 8, 1988, Pat. No. 4,915,863.

[30] Foreign Application Priority Data

Aug. 14, 1987 [JP] Japan ................................. 62-202966
Sep. 9, 1987 [JP] Japan ................................. 62-225870
Sep. 9, 1987 [JP] Japan ................................. 62-225871
Mar. 24, 1988 [JP] Japan ................................. 63-70380
Jul. 5, 1988 [JP] Japan ................................. 63-167157

[51] Int. Cl.$^5$ .................. C07C 255/10; C07C 255/04; C09K 3/00; C01B 15/055
[52] U.S. Cl. ..................................... 558/455; 558/452; 252/186.38; 252/186.2; 252/186.25; 252/102
[58] Field of Search ...................... 252/186.23, 186.22, 252/186.21, 186.38, 186.41, 102, 186.1, 186.2

[56] References Cited

U.S. PATENT DOCUMENTS

| | | | |
|---|---|---|---|
| 2,927,840 | 3/1960 | Dithmar et al. | 252/186.41 X |
| 3,281,452 | 10/1966 | Kapar | 558/455 |
| 3,756,774 | 9/1973 | Kirner et al. | 252/186.29 X |
| 3,882,035 | 5/1985 | Loffelman et al. | 252/186.41 |
| 4,199,466 | 4/1980 | Benson, Jr. | 252/186.41 X |
| 4,211,804 | 7/1980 | Brizzolara | 558/455 |
| 4,297,743 | 1/1967 | Blanchard | 558/453 |
| 4,397,757 | 8/1983 | Bright et al. | 252/186.41 |
| 4,756,845 | 7/1988 | Sugawara et al. | 252/102 |
| 4,818,426 | 4/1989 | Humphreys et al. | 252/186.21 X |
| 4,915,863 | 4/1990 | Aoyagi et al. | 252/186.38 |

FOREIGN PATENT DOCUMENTS

0186052  7/1986  European Pat. Off. .

Primary Examiner—Robert L. Stoll
Assistant Examiner—Joseph D. Anthony
Attorney, Agent, or Firm—Flynn, Thiel, Boutell & Tanis

[57] ABSTRACT

A bleaching composition comprises (a) a peroxide and (b) an organic peracid precursor having at least one group selected from (b-1) and (b-2) and then further comprises a detergent component(s).

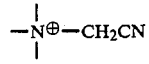

(b-1)

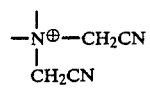

(b-2)

3 Claims, No Drawings

QUATERNARY AMMONIUM SALTS OF DICYANO SUBSTITUTED TERIARY ALKYLENE DIAMINES AS BLEACH ACTIVATORS

This is a division of Ser. No. 07/229,913, filed Aug. 8, 1988 now U.S. Pat. No. 4,915,863.

The present invention relates to a bleach composition and a bleaching detergent composition.

A chlorinated bleaching agent has disadvantages in that it is limited in the kind of fibers to which it is applicable, can not be applied to colored or patterned cloths, and has a peculiar odor. Recently, therefore, an oxygenic bleaching agent free from these disadvantages has been widely used.

Particularly, sodium percarbonate and sodium perborate are generally used as such an oxygenic bleaching agent owing to their excellent bleaching performance and stability.

An oxygenic bleaching agent exhibits a poorer bleaching power than that of a chlorinated bleaching agent, so that various bleach activators are used simultaneously therewith. Further, studies have been made on various activators and examples of them include nitriles such as acetonitrile, malononitrile, phthalonitrile and benzoyliminodiacetonitrile; O-acetates such as glucose pentaacetate, octaacetylsucrose, triacetin, sorbitol hexaacetate, acetoxybenzenesulfonates, triacetyl cyanurate and methyl chloroformate; N-acylates such as N,N,N',N'-tetraacetylethylenediamine, tetraacetylglycolyluril, N-benzylimidazole, di-N-acetyldimethylglyoxime, 1-phenyl-3-acetylhydantoin, N,N-diacetylaniline, N-acetyldiglycolimide and diacetylmethylenediformamide; acid anhydrides such as phthalic anhydride, succinic anhydride, benzoic anhydride, glutaric anhydride, alkylsulfuric anhydride and mixed anhydrides of carboxylic acids and organic sulfonic acids; sulfonyl oximes such as di(methanesulfonyl)dimethylglyoxime; acyl phosphates such as diethyl benzoyl phosphate; phenylsulfonates; organophosphoric azide such as diphenylphosphinic azide; disulfones such as diphenyl disulfone; N-sulfonylimidazole, cyanamide, halogenated triazine and N,N-dimethyl-N-octyl-N-10-carbophenoxydodecylammonium chloride. However, the bleaching power of an oxygenic bleaching agent was poor even when it was used together with an activator described above.

Known compounds having

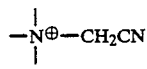

groups in the molecule include the following compounds:

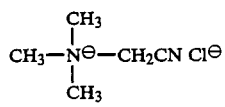

(J. Org. Chem., 1977, Vol. 42, No. 2, pp. 326~332),

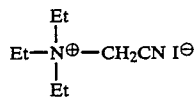

(J. Chem. Soc. Perkin Trans., 2, 1978. No. 8, pp. 786 ~ 793),

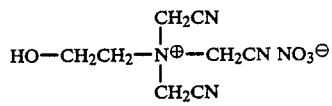

(U.S. Pat. No. 3281452), and

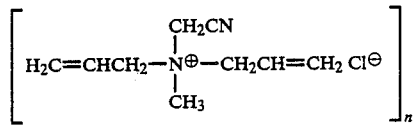

(British Patent No. 1178371).

SUMMARY OF THE INVENTION

The inventors of the present invention have studied for the purpose of developing an oxygenic bleach composition having an enhanced bleaching power and have found that the purpose can be attained by using a peroxide together with a specified cationic organic peracid precursor.

A purpose of the invention is to provide a bleaching composition and a bleaching detergent composition.

Another purpose is to provide a new cationic compound which will serve as an activator for the composition.

The invention provides a bleaching composition which comprises (a) a peroxide and (b) an organic peracid precursor having at least one group selected from (b-1) and (b-2) and then a bleaching detergent composition which further comprises a detergent component(s).

The organic peracid precursor defined above is preferred to include compounds having the generic formulae (b-3), (b-4), (b-5), (b-6) and (b-7), respectively, and then a polyalkylenepolyamine having at least one group of (b-1) and/or (b-2).

These preferable precursors are defined more in detail. A precursor has the generic formula (b-3) in which R1 is a C1 to C24 alkyl, a C1 to C24 alkenyl, an alkaryl having a C1 to C24 alkyl, a C1 to C24 alkyl having a substituent(s), a C1 to C24 alkenyl having a substituent(s), an alkaryl having a C1 to C24 alkyl and another substituent(s), R2 and R3 are each a C1 to C3 alkyl, hydroxyalkyl having 1 to 3 carbon atoms, —(C2-H4O)n H, n being 1 to 5, —CH2—CN and X is an anion.

A precursor has the generic formula (b-4) in which R1 is a C1 to C20 alkyl, a C1 to C20 alkenyl, an aryl, a C1 to C20 alkyl having a substituent(s), a C1 to C20 alkenyl having a substituent(s), an aryl having a substituent(s), R2 and R3 are each a C1 to C3 alkyl, a hydroxyalkyl having 1 to 3 carbon atoms or —(C2-H4O)nH, n being 1 to 3.

A precursor has the genric formula (b-5) or (b-6) in which R1 to R5 are each hydrogen, a C1 to C10 alkyl, a C1 to C10 alkenyl, a C1 to C10 alkyl having a substituent(s), a C1 to C10 alkenyl having a substituent(s), carboxyl, sulfonyl or cyano and X is an anion.

A precursor is an alkylene diamine compound or a polyalkylenepolyamine compound, having at least one group selected from (b-1) and (b-2).

A precursor has the generic formula (b-7) in which R1, R2, R3 and R4 are each a C1 to C6 alkyl, n is an integer of 1 to 16 and X is an anion.

(b-1) 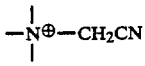

(b-2) 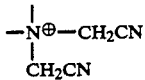

(b-3) 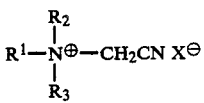

(b-4) 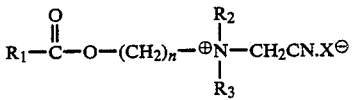

(b-5) 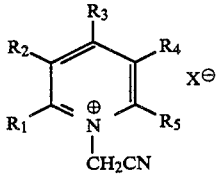

(b-6) 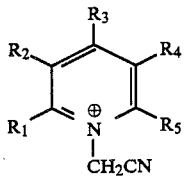

(b-7) 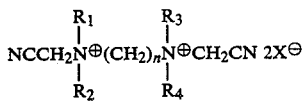

It is preferred that a mole ratio of (a) to (b) ranges from 99.9/0.1 to 20/80 and the component (b) is contained in the composition in the form of granules of a blend of 100 parts by weight of (b) and 5 to 200 parts by weight of a binder.

Then the invention provides a cationic compound having the generic formula (b-7) defined above.

In the invention, the component (b) is required to have a cationic group of

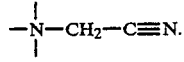

The group (b-2) has two groups of (b-1), however including one cationic nitrogen in common to both groups.

The invention will be below explained in reference to the preferable embodiments of the components (b).

component (b-3)

(b-3) 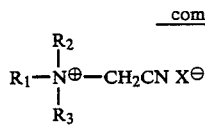

[$R_1$ stands for a straight-chain or branched $C_{1\sim24}$ alkyl or alkenyl group or an alkaryl group (the alkyl group thereof having 1 to 24 carbon atoms), which may be substituted; $R_2$ and $R_3$ each stand for a $C_{1\sim3}$ alkyl or hydroxyalkyl group, $-(C_2H_4O)_{1\sim5}H$ or $-CH_2-CN$ and X is an anion.]

The above ammonium salts can be easily prepared by, for example, the reaction between a corresponding amine and a halogenated nitrile as represented by the following reaction formula:

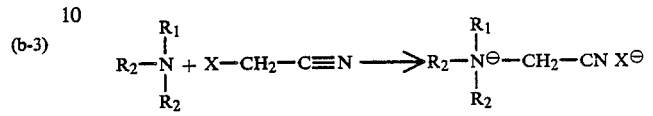

component (b-4)

(b-4) 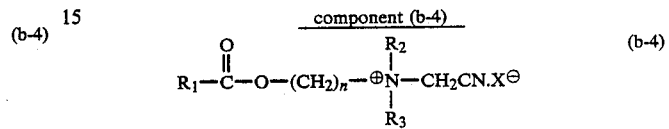

wherein $R_1$ is a straight-chain or branched $C_{1\sim20}$ alkyl, alkenyl or aryl group which may be substituted; $R_2$ and $R_3$ are each an alkyl or hydroxyalkyl group having 1 to 3 carbon atoms or $-(C_2H_4O)_{1\sim5}H$; $X^\ominus$ is an organic or inorganic anion and n is an integer of 1 to 3.

Among the cationic compounds represented by the general formula (b-4) compounds of the formula where in $R_1$ is an alkyl group having 1 to 8 carbon atoms or a phenyl group and n is 2 are most preferred as a bleach activator.

The cationic compound represented by the general formula (b-4) can be prepared by, for example, the following process. Namely, it can be prepared by the reaction between a tertiary amine and a halogenated acetonitrile in a similar manner to that of an ordinary conversion of an amine into a corresponding quaternary ammonium compound.

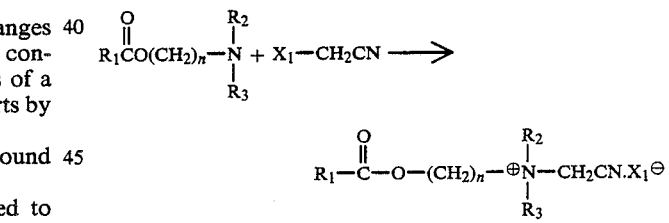

compound (b-5) and (b-6)

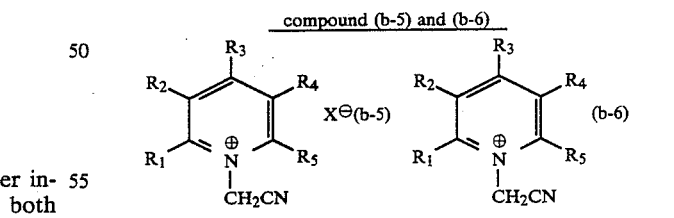

wherein $R_{1-5}$ each stand for a hydrogen atom, a straight-chain or branched $C_{1-10}$ alkyl or alkenyl group which may be substituted or a carboxyl, sulfonyl or cyano group and $X^-$ stands for an organic or inorganic anion.

The ammonium salt to be used in the present invention can be easily prepared by, for example, the reaction between a corresponding pyridine which is arbitrarily substituted with an alkyl, alkenyl, carboxyl, sulfonyl or cyano grop and a halogenated nitrile as represented by the following reaction formula:

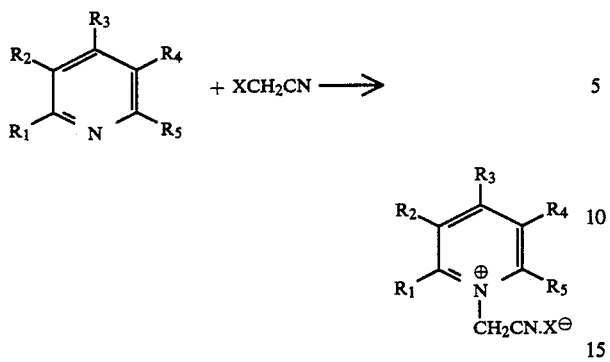

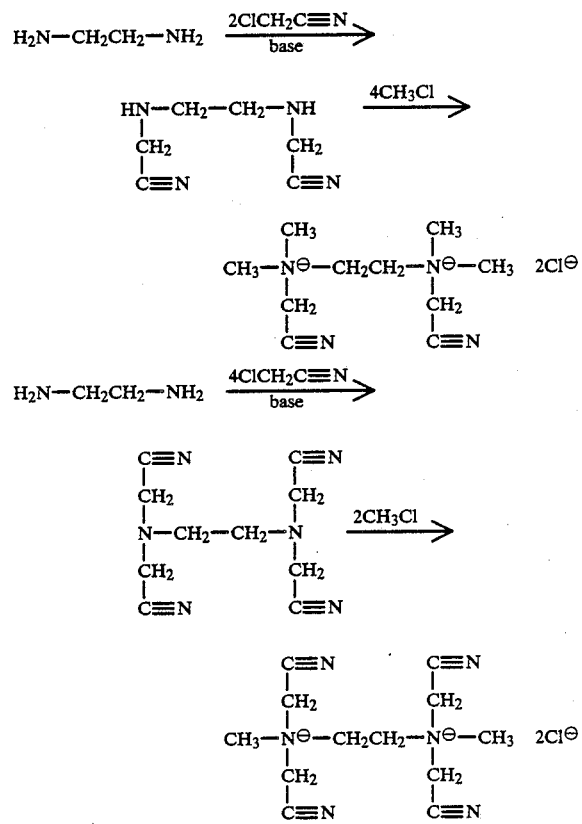

The pyridine to be used as a starting material, which is arbitrarily substituted with an alkyl, alkenyl, carboxyl, sulfonyl or cyano group, includes pyridine, 2-, 3- and 4- picolinic acids, nicotinic acid, 3,5-pyridinecarboxylic acid, 3-pyridinesulfonic acid, and 2-, 3- and 4-cyanopyridines, among which pyridine and nicotinic acid are most preferred owing to their high effect.

ALKYLENEDIAMINE COMPOUND AND POLYALKYLENEPOLYAMINE COMPOUND

It has at least one group selected from the above shown (b-1) and (b-2) and in other words at least one quaternary nitrogen atom shown in the formula (b-1) or (b-2).

The activator according to the present invention is derived from alkylenediamine or polyalkylenepolyamine. Particularly, alkylenediamines and polyalkylenepolyamines represented by the general formula:

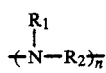

(wherein $R_1$ is a hydrogen atom or a lower alkyl group; $R_2$ is a straight-chain or branched $C_{2\sim10}$ alkylene group and n is 2 to 1,000) are useful as starting materials of the activators according to the present invention. A particular example of the alkylenediamine includes ethylenediamine, while examples of the polyalkylenepolyamine include relatively low-molecular weight polyethylenepolyamines having a molecular weight of up to 1000, such as diethylenetriamine, triethylenetetramine and tetraethylenepentamine, tripropylenetetramine, tetrabutylenepentamine, dibutylenetriamine, dihexylenetriamine and trihexylenetetramine.

The introduction of the group of

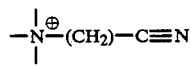

can be easily carried out by reacting the nitrogen atom of an alkylenediamine or polyalkylenepolyamine with a compound represented by the general formula: X'—(CH$_2$)—C≡N (X' is a halogen atom) to thereby form a quaternary ammonium compound, preferably chloroacetonitrile from the viewpoint of cost and availability.

Processes for preparing the activator of the present invention from ethylenediamine as a starting material will now be described.

These processes are only examples of the process for the preparation of the activator according to the present invention, so that the activator can be also prepared by processes other than those described above. The alkylenediamine or polyalkylenepolyamine to be used as a starting material may be either primary like those shown in the above examples or secondary or tertiary. The structure of the obtained activator varies depending upon the molar ratios of the chloroacetonitrile and alkyl halide used to the alkylenediamine or polyalkylenepolyamine as the starting material, so that various activators can be prepared.

In short, the activator according to the present invention corresponds to alkylenediamine or polyalkylenepolyamine wherein at least one, preferably at least two, nitrogen atom thereof is converted into a group of a structure represented by the formula:

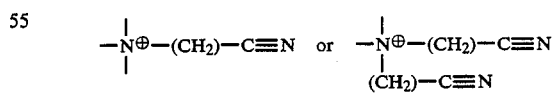

COMPOUND (b-7)

This is most preferable component (b).

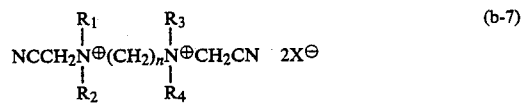

wherein $R_1$, $R_2$, $R_3$ and $R_4$ each stand for an alkyl group having 1 to 6 carbon atoms, $X^\ominus$ stands for an organic or inorganic anion, and n is an integer of 1 to 16.

Of the novel compounds of the present invention, those of the formula (b-7) in which $R_1$, $R_2$, $R_3$ and $R_4$ each stand for an alkyl group having 1 to 3 carbon atoms, especially a methyl group, and n is an integer of 1 to 9 are especially valuable.

The compound of the general formula according to the present invention can be prepared, for example, according to the process described below. Namely, the compound of the formula can be easily preared by reacting a tertiary alkylenediamine with a halide of acetonitrile as in the quaternization of an ordinary amine, as shown by the following reaction formula:

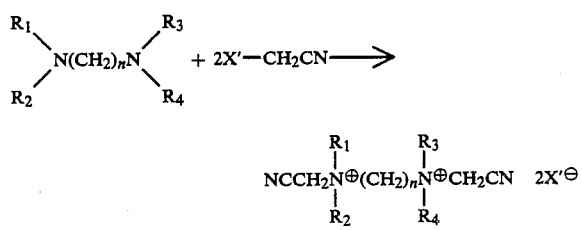

The compound (b-7) is novel and useful as a textile softener, an antistatic agent, a fungicide and a bleaching activator.

In the invention, the component (b) is easy to adhere on articles to bleach, owing to its cationic group. In addition, the carbon atom in the group —CN is easy to be positive electrically and active to the bleaching effect since the quaternary nitrogen is electron-attractive. This way the component (b) serves to provide for sites where bleaching takes place to the effect and enhance the bleaching power of the composition.

The activator according to the present invention can be granulated by an ordinary method prior to its addition to a peroxide. For example, 5 to 200 parts by weight, preferably 10 to 100 parts by weight, of one or more binders exhibiting a fluidity at 5° to 60° C., preferably 10° to 40° C., is added to 100 parts by weight of an activator and the obtained mixture is granulated.

The binder to be used may be one or more members selected from among nonionic surfactants polyethylene glycol, polypropylene glycol, liquid paraffins and higher alcohols which exhibit a fluidity at 5° to 60° C., preferably 10° to 40° C.

The granulation may be carried out by a method selected depending upon the kinds of the organic per acid precursor and binder used from among conventional methods such as extruding granulation, tumbling granulation or compression granulation. For example, according to the extruding granulation, an organic per acid precursor which has been finely ground into a size of 150 μm or below is homogeneously mixed by means of an ordinary mixer and a binder is gradually added to the ground precursor, followed by sufficient kneading. Then, the kneaded mixture was fed into an extruding granulator to obtain a granulate, followed by screening. If necessary, the granulate may be coated, prior to the screening, with a fine inorganic powder having an average primary particle size of 0.1 μm or below, such as finely powdered silica, for the purpose of improving the granular characteristics.

The peroxide to be used in the present invention is preferably hydrogen peroxide or a peroxide which generates hydrogen peroxide in an aqueous solution.

Examples of the peroxide which generates hydrogen peroxide in an aqueous solution include sodium carbonate-hydrogen peroxide adduct, sodium tripolyphosphate-hydrogen peroxide adduct, sodium pyrophosphate-hydrogen peroxide adduct, urea-hydrogen peroxide adduct, $4Na_2SO_4.2H_2O_2.NaCl$, sodium perborate monohydrate, sodium perborate tetrahydrate, sodium peroxide and calcium peroxide, among which sodium carbonate-hydrogen peroxide adduct, sodium perborate monohydrate and sodium perborate tetrahydrate are particularly preferred.

According to the present invention, a peroxide and a specified activator as defined above are generally used in a molar ratio of said peroxide to said activator of between 99.1:0.1 and 20:80, preferably between 99:1 and 50:50. It is preferable that the composition comprises 1 to 99 percent by weight of the component (a).

The bleaching detergent composition of the invention may comprises the following in addition to the above shown bleaching agents.

[1] Surfactants:

(1) Straight-chain or branched alkylbenzenesulfonate salts having an alkyl group of 10–16 carbon atoms in average.

(2) Alkyl or alkenyl ether sulfate salts having a straight-chain or branched alkyl or alkenyl group of 10–20 carbon atoms in average, 0.5–8 mol in average of ethylene oxide, propylene oxide or butylene oxide in the molecule and an addition ratio of ethylene oxide/propylene oxide of 0.1/9.9–9.9/0.1 or ethylene oxide/butylene oxide of 0.1/9.9–9.9/0.1.

(3) Alkyl or alkenyl sulfate salts having an alkyl or alkenyl group of 10–20 carbon atoms in average.

(4) Olefinsulfonate salts having 10–20 carbon atoms in average in the molecule.

(5) Alkanesulfonate salts having 10–20 carbon atoms in average in the molecule.

(6) Saturated or unsaturated fatty acid salts having 10–24 carbon atoms in average in the molecule.

(7) Alkyl or alkenyl ether carboxylate salts having an alkyl or alkenyl group of 10–20 carbon atoms in average, 0.5–8 mol in average of ethylene oxide, propylene oxide or butylene oxide in the molecule and an addition ratio of ethylene oxide/propylene oxide of 0.1/9.9–9.9/0.1 or ethylene oxide/butylene oxide of 0.1/9.9 to 9.9/0.1.

(8) α-Sulfo fatty acid salts or esters of the general formula:

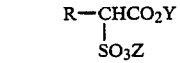

wherein Y represents an alkyl group having 1–3 carbon atoms or a counter-ion, Z represents a counter-ion and R represents an alkyl or alkenyl group having 10–20 carbon atoms.

As the counter-ions of anionic surfactants, there may be mentioned, for example, ions of alkali metals such as sodium and potassium, alkaline earth metals such as calcium and magnesium, ammonium, alkanolamines containing 1–3 alkanol groups having 2 or 3 carbon atoms such as monoethanolamine, diethanolamine, triethanolamine and triisopropanolamine.

(9) Amino acid-type surfactants of the general formulae:

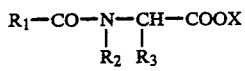
No. 1 wherein $R_1$ represents an alkyl or alkenyl group having 8–24 carbon atoms, $R_2$ represents hydrogen or an alkyl group having 1–2 carbon atoms, $R_3$ represents an amino acid residue and X represents an alkali metal or alkaline earth metal ion.

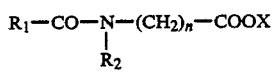
No. 2 wherein $R_1$, $R_2$ and X have the same meanings as above and n represents an integer of 1–5.

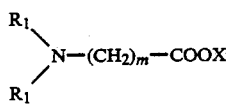
No. 3 wherein $R_1$ has the same meaning as above and m represents an integer of 1–8.

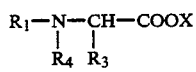
No. 4 wherein $R_1$, $R_3$ and X have the same meaning as above and $R_4$ represents hydrogen, or an alkyl or hydroxyalkyl group having 1–2 carbon atoms.

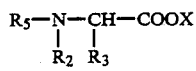
No. 5 wherein $R_2$, $R_3$ and X have the same meaning as above and $R_5$ represents a β-hydroxyalkyl or β-hydroxyalkenyl group having 6–28 carbon atoms.

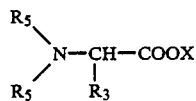
No. 6 wherein $R_3$, $R_5$ and X have the same meaning as above.

(10) Phosphate ester surfactants:
No. 1 Acid alkyl (or alkenyl) phosphates:

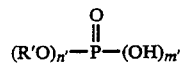

wherein R′ represents an alkyl or alkenyl group having 8–24 carbon atoms, n′+m′ represents 3 and n′ represents a number of 1–2.

No. 2 Alkyl (or alkenyl) phosphates:

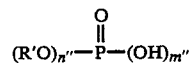

wherein R′ has the same meaning as above, n″+m″ represents a number of 3 and n″ represents a number of 1–3.

No. 3 Alkyl (or alkenyl) phosphate salts:

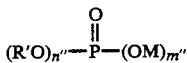

wherein R′, n″ and m″ have the same meaning as above and M represents Na, K or Ca.

(11) Sulfonic acid-type amphoteric surfactants of the general formulae:

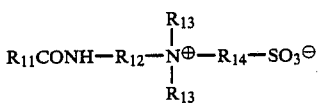
No. 1 wherein $R_{11}$ represents an alkyl or alkenyl group having 8–24 carbon atoms, $R_{12}$ represents an alkylene group having 1–4 carbon atoms, $R_{13}$ represents an alkyl group having 1–5 carbon atoms, $R_{14}$ represents an alkylene or hydroxyalkylene group having 1–4 carbon atoms.

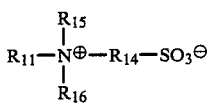
No. 2 wherein $R_{11}$ and $R_{14}$ have the same meaning as above and $R_{15}$ and $R_{16}$ each represent an alkyl or alkenyl group having 8–24 or 1–5 carbon atoms.

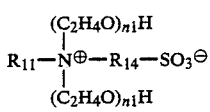
No. 3 wherein $R_{11}$ and $R_{14}$ have the same meaning as above and n1 represents an integer of 1–20.

(12) Betaine-type, amphoteric surfactants of the general formulae:

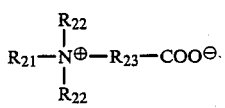
No. 1 wherein $R_{21}$ represents an alkyl, alkenyl, β-hydroxyalkyl or β-hydroxyalkenyl group having 8–24 carbon atoms, $R_{22}$ represents an alkyl group having 1–4 carbon atoms and $R_{23}$ represents an alkylene or hydroxyalkylene group having 1–6 carbon atoms.

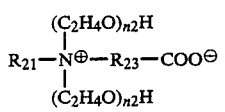
No. 2 wherein $R_{21}$ and $R_{23}$ have the same meaning as above and n2 represents an integer of 1–20.

$$R_{21}-\overset{R_{24}}{\underset{R_{24}}{N^{\oplus}}}-R_{23}-COO^{\ominus} \qquad \text{No. 3}$$

wherein $R_{21}$ and $R_{23}$ have the same meaning as above and $R_{24}$ represents a carboxyalkyl or hydroxyalkyl group having 2-5 carbon atoms.

(13) Polyoxyethylene alkyl or alkenyl ethers having an alkyl or alkenyl group of 10-20 carbon atoms in average and 1-30 mol of ethylene oxide added.

(14) Polyoxyethylene alkylphenyl ethers having an alkyl group of 6-12 carbon atoms in average and 1-25 mol of ethylene oxide added.

(15) Polyoxypropylene alkyl or alkenyl ethers having an alkyl or alkenyl group of 10-20 carbon atoms in average and 1-20 mol of propylene oxide added.

(16) Polyoxybutylene alkyl or alkenyl ethers having an alkyl or alkenyl group of 10-20 carbon atoms in average and 1-20 mol of butylene oxide added.

(17) Nonionic surfactants having an alkyl or alkenyl group of 10-20 carbon atoms in average and 1-30 mol in total of ethylene oxide and propylene oxide added or ethylene oxide and butylene oxide added (ratio of ethylene oxide to propylene oxide or butylene oxide being 0.1/9.9 to 9.9/0.1).

(18) Higher fatty acid alkanolamides or alkylene oxide adducts thereof of the general formula:

$$R'_{11}CON\begin{matrix}(CHCH_2O)_{n3}H \\ | \\ R'_{12} \\ \\ (CHCH_2O)_{m3}H \\ | \\ R'_{12}\end{matrix}$$

wherein $R'_{11}$ represents an alkyl or alkenyl group having 10-20 carbon atoms, $R'_{12}$ represents H or $CH_3$, n3 represents an integer of 1-3 and m3 represents an integer of 0-3.

(19) Sucrose/fatty acid esters comprising fatty acids having 10-20 carbon atoms in average and sucrose.

(20) Fatty acid/glycerol monoesters comprising fatty acids having 10-20 carbon atoms in average and glycerol.

(21) Alkylamine oxides of the general formula:

$$R'_{13}-\overset{R'_{14}}{\underset{R'_{15}}{N}}\rightarrow O$$

wherein $R'_{13}$ represents an alkyl or alkenyl group having 10-20 carbon atoms and $R'_{14}$ and $R'_{15}$ each represent an alkyl group having 1-3 carbon atoms.

(22) Cationic surfactants of the general formulae:

$$[R'_1-\overset{R'_2}{\underset{R'_3}{N^{\oplus}}}-R'_4]X'^{\ominus} \qquad \text{No. 1}$$

wherein at least one of $R'_1$, $R'_2$, $R'_3$ and $R'_4$ represents an alkyl or alkenyl group having 8-24 carbon atoms and the remainder represents an alkyl group having 1-5 carbon atoms and X' represents a halogen.

$$[R'_1-\overset{R'_2}{\underset{R'_3}{N^{\oplus}}}-CH_2C_6H_5]X'^{\ominus} \qquad \text{No. 2}$$

wherein $R'_1$, $R'_2$, $R'_3$ and X' have the same meaning as above.

$$[R'_1-\overset{(R'_5O)_{n4}H}{\underset{(R'_5O)_{n4}H}{N^{\oplus}}}-R'_2]X'^{\ominus} \qquad \text{No. 3}$$

wherein $R'_1$, $R'_2$ and X' have the same meaning as above, $R'_5$ represents an alkylene group having 2-3 carbon atoms and n4 represents an integer of 1-20.

The composition probably contains at least one of the above surfactants in an amount of at least 10 wt. %.

As preferred surfactants, there may be mentioned above surfactants (1), (2), (3), (4), (5), (6), (11)-No. 2, (12)-No. 1, (13), (14), (15), (17) and (18).

[2] Divalent metal ion sequestering agents:

The composition may contain 0-50 wt. % of one or more builder components selected from the group consisting of alkali metal salts or alkanolamine salts of the following compounds:

(1) Salts of phosphoric acids such as orthophosphoric acid, pyrophosphoric acid, tripolyphosphoric acid, metaphosphoric acid, hexametaphosphoric acid and phytic acid.

(2) Salts of phosphonic acids such as ethane-1,1-diphosphonic acid, ethane-1,1,2-triphosphonic acid, ethane-1-hydroxy-1,1-diphosphonic acid and its derivatives, ethane-hydroxy-1,1,2-triphosphonic acid, ethane-1,2-dicarboxy-1,2-diphosphonic acid and methanehydroxyphosphonic acid.

(3) Salts of phosphono carboxylic acids such as 2-phosphonobutane-1,2-dicarboxylic acids, 1-phosphonobutane-2,3,4-tricarboxylic acids and α-methylphosphonosuccinic acid.

(4) Salts of amino acids such as aspartic acid, glutamic acid and glycine.

(5) Salts of aminopolyacetic acids such as nitrilotriacetic acid, iminodiacetic acid, ethylenediaminetetraacetic acid, diethylenetriaminepentaacetatic acid, glycol ether diaminetetraacetic acid, hydroxyethyliminodiacetic acid, triethylenetetraminehexaacetic acid and dienkolic acid.

(6) High-molecular electrolytes such as polyacrylic acid, polyaconitic acid, polyitaconic acid, polycitraconic acid, polyfumaric acid, polymaleic acid, polymesaconic acid, poly-α-hydroxyacrylic acid, polyvinylphosphonic acid, sulfonated polymaleic acid, maleic anhydride/diisobutylene copolymer, maleic anhydride/styrene copolymer, maleic anhydride/methyl vinyl ether copolymer, maleic anhydride/ethylene copolymer, maleic anhydride/ethylene cross-linked copolymer, maleic anhydride/vinyl acetate copolymer, maleic anhydride/acrylonitrile copolymer, maleic anhydride/acrylate ester copolymer, maleic anhydride/butadiene copolymer, maleic anhydride/isoprene copolymer, poly-β-keto carboxylic acid derived from maleic anhydride and carbon monoxide, itaconic acid/ethylene copolymer, itaconic acid/aconitic acid copolymer, itaconic acid/maleic acid copolymer, itaconic acid/acrylic acid copolymer, malonic acid/methylene copolymer, mesaconic acid/fumaric acid copolymer, ethylene glycol/ethylene terephthalate copolymer, vinylpyrrolidone/vinyl acetate copolymer, 1-butene-2,3,4-tricarboxylic acid/itaconic acid/acrylic acid copolymer, quaternary ammonium group-containing polyester polyaldehyde carboxylic acids, cis-isomer of epoxysuccinic acid, poly[N,N-bis(carboxymethyl)acrylamide], poly(hydroxy carboxylic acid), starch succinate, starch maleate, starch terephtalate, starch phosphate ester, dicarboxystarch, dicarboxymethylstarch and cellulose succinate esters.

(7) Non-dissociating high-molecular compounds such as polyethylene glycol, polyvinyl alcohol, polyvinylpyrrolidone and cold water-soluble, urethanated polyvinyl alcohol.

(8) Salts of dicarboxylic acids such as oxalic acid, malonic acid, succinic acid, glutaric acid, adipic acid, pimelic acid, suberic acid, azelaic acid and decane-1,10-dicarboxylic acid; salts of diglycolic acid, thiodiglycolic acid, oxalacetic acid, hydroxydisuccinic acid, carboxymethylhydroxysuccinic acid and carboxymethyltartronic acid; salts of hydroxy carboxylic acids such as glycolic acid, malic acid, hydroxypivalic acid, tartaric acid, citric acid, lactic acid, gluconic acid, mucic acid, glucuronic acid and dialdehydostarch oxide; salts of itaconic acid, methylsuccinic acid, 3-methylglutaric acid, 2,2-dimethylmalonic acid, maleic acid, fumaric acid, glutamic acid, 1,2,3-propanetricarboxylic acid, aconitic acid, 3-butene-1,2,3-tricarboxylic acid, butane-1,2,3,4-tetracarboxylic acid, ethanetetracarboxylic acid, ethenetetracarboxylic acid, n-alkenylaconitic acid, 1,2,3,4-cyclopentanetetracarboxylic acid, phthalic acid, trimesic acid, hemimellitic acid, pyromellitic acid, benzenehexacarboxylic acid, tetrahydrofuran-1,2,3,4-tetracarboxylic acid and tetrahydrofuran-2,2,5,5-tetracarboxylic acid; salts of sulfonated carboxylic acids such as sulfoitaconic acid, sulfotricarballylic acid, cysteic acid, sulfoacetic acid and sulfosuccinic acid; carboxymethylated sucrose, lactose and raffinose, carboxymethylated pentaerythritol, carboxymethylated gluconic acid, condensates of polyhydric alcohols or saccharides with maleic anhydride or succinic anhydride, condensates of hydroxy carboxylic acids with maleic anhydride or succinic anhydride, and organic acid salts such as CMOS and Builder M.

(9) Aluminosilicates:

No. 1 Crystalline aluminosilicates of the formula:

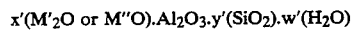

wherein M' represents an alkali metal atom, M" represents an alkaline earth metal atom exchangeable with calcium, and x', y' and w' represent mole numbers of the respective components and generally, they are as follows: $0.7 \leq x' \leq 1.5$, $0.8 \leq y' \leq 6$ and w' being a positive number.

No. 2 Detergent builders having the following general formula are particularly preferred:

$$Na_2O \cdot Al_2O_3 \cdot nSiO_2 \cdot wH_2O$$

wherein n represents a number of 1.8-3.0 and w represents a number of 1-6.

No. 3 Amorphous aluminosilicates of the formula:

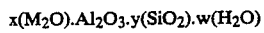

wherein M represents sodium and/or potassium atom, and x, y and w represent mole numbers of the respective components within the following ranges:

$$0.7 \leq x \leq 1.2$$

$$1.6 \leq y \leq 2.8$$

w: any positive number including 0.

No. 4 Amorphous aluminosilicates of the formula:

wherein M represents Na or K and X, Y, Z and ω represent mole numbers of the respective components within the following ranges:

$$0.20 \leq X \leq 1.10$$

$$0.20 \leq Y \leq 4.00$$

$$0.001 \leq Z \leq 0.80$$

ω: any positive number including 0.

[3] Alkalis or inorganic electrolytes:

The composition may contain also 1-50 wt. %, preferably 5-30 wt. %, of one or more alkali metal salts selected from the following compounds as the alkali or inorganic electrolyte: silicates, carbonates and sulfates. Further, the composition may contain organic alkalis such as triethanolamine, diethanolamine, monoethanolamine and triisopropanolamine.

[4] Antiredeposition agents:

The composition may contain 0.1-5% of one or more of the following compounds as antiredeposition agent(s): polyethylene glycol, polyvinyl alcohol, polyvinylpyrrolidone and carboxymethylcellulose.

[5] Enzymes (enzymes which exhibits the essential enzymatic effects thereof in the deterging step):

As the enzymes, the following enzymes may be mentioned (classified with respect to their enzymatic reactivities):

Hydrolases, hydrases, oxido-reductases, desmolases, transferases and isomerases. All of these enzymes may be used in the present invention. Particularly preferred enzymes are hydrolases auch as proteases, esterases, carbohydrolases and nucleases.

Examples of proteases are pepsin, trypsin, chymotrypsin, collagenase, keratinase, elastase, subtilisin, BPN, papain, bromelin, carboxypeptidases A and B, aminopeptidase and aspergillopeptidases A and B.

Examples of esterases are gastric lipase, pancreatic lipase, vegetable lipases, phospholipases, cholinesterases and phosphotases.

Carbohydrolases include alkali cellulases, maltase, saccharase, amylase, pectinase, lysozyme, α-glucosidase and β-glucosidase.

[6] Bluing agents and fluorescent dyes:

Various bluing agents and fluorescent dyes may be incorporated in the composition, if necessary. For example, compounds of the following structures are recommended:

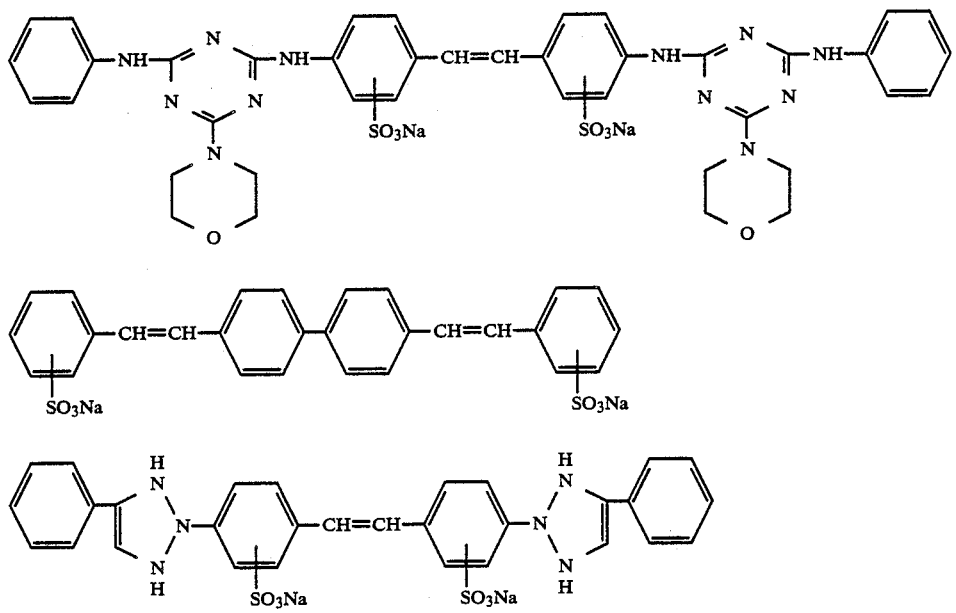

and bluing agents of the general formulae:

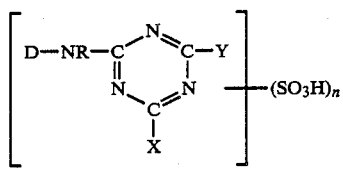

wherein D represents a residue of blue or purple, monoazo, disazo or anthraquinone dye, X and Y each represent hydroxyl group, amino group, an aliphatic amino group which may be substituted with hydroxyl, sulfonic acid, carboxylic acid or alkoxyl group, or an aromatic or alicyclic amino group which may be substituted with a halogen atom or hydroxyl, sulfonic acid, carboxylic acid, lower alkyl or lower alkoxyl group, R represents a hydrogen atom or a lower alkyl group but excluding cases wherein (1) R represents a hydrogen atom and both X and Y represents a hydroxyl group or an alkanolamine at the same time and (2) R represents a hydrogen atom, one of X and Y represents a hydroxyl group and the other represents an alkanolamine group, and n represents an integer of at least 2, and

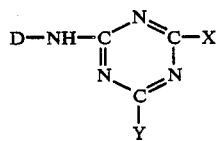

wherein D represents a residue of a blue or purple, azo or anthraquinone dye, and X and Y may be the same or different and represent an alkanolamine residue or a hydroxyl group.

[7] Caking-preventing agents:

The following caking-preventing agents may be incorporated in powdery detergent composition: p-toluenesulfonate salts, xylenesulfonate salts, acetate salts, sulfosuccinate salts, talc, finely pulverized silica, clay, calcium silicates (such as Micro-Cell of Johns-Manvill Co.), calcium carbonate and magnesium oxide.

[8] Antioxidants:

The antioxidants include, for example, tert-butylhydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1'-bis(4-hydroxyphenyl)cyclohexane.

[9] Stabilizer for the peroxide and an adduct to hydrogen peroxide

A stabilizer may be used in the bleaching detergent composition, including a magnesium salt such as magnesium sulfate, magnesium silicate, magnesium chloride, magnesium silicofluoride, magnesium oxide and magnesium hydroxide and a silicate such as sodium silicate.

[10] Fragrant matter and Coloring matter

EXAMPLE

The invention will be illustrated below in reference to preparation of the component (b) and then the bleaching composition. Nine compounds for the component (b) were produced, I-a and I-b falling with the definition (b-3), II-a and II-b falling with (b-4), III-a and III-b falling within (b-5) and (b-6), respectively, (IV-a) and (IV-b) falling within (b-7) and (IV-c) falling within the definition of the polyalkylenepolyamine compound.

PRODUCTION EXAMPLE 1

Synthesis of

Chloroacetonitrile was dissolved in 20 cc of acetone in a 100-ml three-necked flask. Dry trimethylamine was bubbled into the solution by using nitrogen as a carrier gas, while stirring the solution with a magnet stirrer. After the bubbling had been continued over a period of 3 hours to thereby introduce twice by equivalent as much trimethylamine as chloroacetonitrile, the flask was sealed and stirred at a room temperature overnight. The generated white crystal was separated by filtration to give 8.93 g of the compound (I-a). Yield: 95.3%

PRODUCTION EXAMPLE 2

Synthesis of

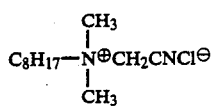 (I-b)

10.7 g of dimethyloctylamine was dissolved in 20 ml of ethanol in a 100-ml two-necked flask fitted with a cooling tube, followed by the dropwise addition of 5.42 g of chloroacetonitrile. After the completion of the dropwise addition, the mixture was heated on an oil bath (temperature: 90° C.) to carry out the reaction under the reflux of the ethanol, until the disappearance of the starting amine was confirmed by TLC. The resulting reaction mixture was distilled to remove the ethanol to obtain 15.76 g of a quaternary salt of the above formula. Yield: 99.3%

PRODUCTION EXAMPLE 3

Synthesis of

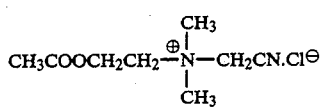 (II-a)

6.0 g of 2-dimethylaminoethyl acetate was dissolved in 20 ml of acetone in a 100-ml two-necked flask. 8.6 g of chloroacetonitrile was dropwise added to the flask at a room temperature. The obtained mixture was stirred at that temperature for 8 hours and distilled to remove the solvent. The residue was sufficiently washed with acetone and distilled to remove the acetone. Thus, 7.3 g of the cationic compound was obtained as a colorless oil. Yield: 93%

Physical properties
IR(KBr, cm$^{-1}$) 3382, 3016, 2968, 2908, 1746, 1479, 1377, 1233, 1050.
'H-NMR (CD$_3$OD, TMS as internal reference, $\sigma$) 2.48 (3H, s), 3.83 (6H, s), 4.25~4.4 (2H, t), 4.68~4.85 (2H, t), 5.4 (2H, s).

PRODUCTION EXAMPLE 4

Synthesis of

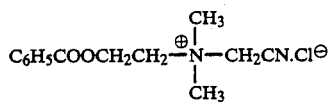 (II-b)

5 g of 2-dimethylaminoethyl benzoate was dissolved in 20 ml of acetone in a 100-ml two-necked flask. 5.9 g of chloroacetonitrile was dropwise added to the flask at a room temperature. The obtained mixture was stirred at that temperature for 8 hours and filtered to give white crystals. The crystals were washed with acetone and dried to give 6.17 g of the cationic compound as a colorless crystal. Yield: 89%

Physical properties
mp 177°–180° C.

IR(KBr, cm$^{-1}$) 3028, 2920, 1722, 1488, 1470, 1446, 1371, 1314, 1269, 1170, 1113, 1065, 1026, 975, 915, 894, 708.
'H-NMR (CD$_3$OD, TMS as internal reference, $\sigma$) 3.9 (6H, s), 4.4~4.6 (2H, t), 5.05~5.25 (2H, t), 7.8~8.0 (2H, d), 8.35~8.55 (2H, d).

PRODUCTION EXAMPLE 5

The compound (III-a) was synthesized.

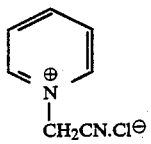 (III-a)

Ten grams of pyridine was dissolved in 20 cc of acetone. Then 14.3 g of chloroacetonitrile was added dropwise to the solution, while stirred. The mixture continued to be stirred for 8 hours at room temperature. The reaction product mixture was found to be lightly brown and 18.0 grams of the compound (III-a) was isolated from it with a production yield of 92.3 percent.

PRODUCTION EXAMPLE 6

The compound (III-b) was synthesized.

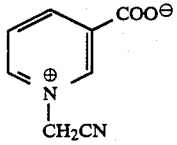 (III-b)

Ten grams of nicotinic acid and 3.4 g of NaOH in combination were dissolved in 100 ml of methanol with a flask equipped with a cooling tube. Then 9.2 g of chloroacetonitrile was added dropwise to the solution. The reaction mixture was heated with an oil bath of 80° C. and the reaction continued for 3 hours while methanol was being refluxed. After the solvent had been distilled out, the product (III-b) was obtained by recrystallization in methanol, in an amount of 7.1 g, with a production yield of 54 percent.

PRODUCTION EXAMPLE 7

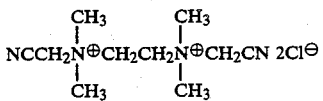 (IV-a)

In 100-ml of acetone was dissolved 20 g (172 mmol) of chloroacetonitrile and, while the solution was stirred at room temperature in a 300-ml two-necked flask equipped with a reflux tube by means of a magnetic stirrer, a solution of 39 g (516 mmol) of N,N,N',N'-tetramethylethylenediamine in 100-ml of acetone was dropped into the solution. After the completion of the dropwise addition, the mixture was heated at 90° C. and reacted for 90 minutes, followed by concentration and cooling. The formed crystal was recovered by filtration to give 39.37 g of the compound (I-a). The yield was 85.6%.

Melting point: 195° to 200° C. (dec.).

$\nu_{KBr}$ (cm$^{-1}$): 3022, 2944, 1482, 1455, 1410, 981, 918, 906, 792.

$^1$H-NMR: 3.52 (12H, s), 4.33 (4H, s), 4.95 (4H, brs).

PRODUCTION EXAMPLE 8

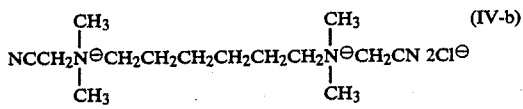

Production Example 7 was followed in the same manner except that 57.8 g (516 mmol) of N,N,N',N'-tetramethyl-1,6-hexanediamine was used instead of 39 g of tetramethylethylenediamine, whereby 102.8 g of the compound (IV-b) was prepared in the form of a white crystal. The yield was 80.3%.

Melting point: 201° to 203° C. (dec.).

$\nu_{KBr}$ (cm$^{-1}$): 2962, 2920, 1488, 1455.

$^1$H-NMR: 1.05–2.25 (8H, m), 3.35 (12H, s), 3.40–3.80 (4H, m), 4.75 (4H, s).

PRODUCTION EXAMPLE 9

Synthesis of (IV-c)

100 g of an amine represented by the formula:

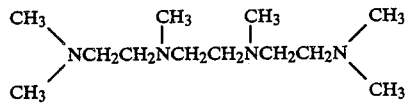

was dissolved in 400 cc of ethanol in a 1000-ml three-necked flask fitted with a cooling tube to give a solution. 131.3 g of chloroacetonitrile was dropwise added to the solution. After the completion of the dropwise addition, the temperature of the obtained mixture was raised with an oil bath (temperature: 90° C.). The resulting mixture was heated under reflux of the ethanol for 24 hours and distilled to remove the ethanol. Thus, 177.3 g of a quaternary ammonium salt of the above amine was obtained. Conversion into quaternary ammonium salts: 76.6%

EXAMPLES 1 TO 8 OF COMPOSITION

Bleaching compositions were prepared, shown in Table 1, using the organic peracid precursors I-a to IV-c, with control compositions 1 to 4, and tested on their bleaching effect in terms of a bleaching rate or a bleaching extent. Results are shown in Table 1.

Dip Bleaching Effect (Table 1)

Sodium percarbonate was dissolved in 300 ml of water of 20° C. to prepare a solution having an active oxygen content of 0.05%. An activator was added to the solution in such a way that one sixteenth of the equivalent amount of the hydrogen peroxide contained in the solution was equal to the equivalent amount of the C≡N group of the activator. Thus, a bleach composition was obtained. Five black tea-stained cloths (8×8 cm$^2$) which had been prepared by the method which will be described below were soaked in the bleach composition for 30 minutes, washed with water and dried. The rate of bleaching was calculated by the following equation: rate of bleaching with respect to black tea-stained cloth:

$$\text{rate of bleaching (\%)} = \frac{\text{reflectance after bleaching} - \text{reflectance before bleaching}}{\text{reflectance of white cloth} - \text{reflectance before bleaching}} \times 100$$

These reflectances were determined with NDR-101DP mfd. by Nippon Denshoku Kogyo K.K. by the use of a filter of 460 nm. Black tea-stained cloth:

80 g of NITTOH black tea (yellow package) was boiled in 3 l of ion-exchanged water for about 15 minutes and the resulting mixture was filtered through a desized bleached cotton cloth. A cotton shirting cloth #2003 was immersed in the obtained filtrate and boiled for about 15 minutes. The cloth immersed in the filtrate was taken off as such from fire and allowed to stand for about 2 hours. The resulting cloth was spontaneously dried and washed with water until the washings became colorless. The resulting cloth was dehydrated and pressed to form a test piece (8×8 cm).

In Table 1, the compound shown (1) has the formula:

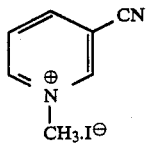

TAED shown (2) is tetraacetylethylenediamine being available from Hoechst. The compound shown (3) is available Interox. The bleaching extent shown (4) is measured with a solution having an active oxygen concentration of 0.05%.

EXAMPLES 9 AND 10 OF COMPOSITION

Bleaching Method

Hydrogen peroxide was added to 300 ml of water at 20° C. so that the effective oxygen concentration was 0.05%, and 1 g of sodium carbonate was further added thereto. The compound (IV-a) or (IV-b) was added to the solution in an amount equimolar to hydrogen peroxide. A black tea stained cloth prepared in the same way as before, having a size of 10 cm and 10 cm, was immersed in the solution for 30 minutes to effect bleaching. The cloth was washed with water and dried, and the bleaching ratio was calculated according to the formula described below. Sodium hypochlorite as a comparative product was evaluated at an effective chlorine concentration of 0.06%. Results are shown in Table 2.

EXAMPLES 11 TO 18 OF DETERGENT COMPOSITION

Sodium percarbonate and cationic compounds shown in Table 3 were added to a solution of a heavyduty detergent comprising a nonionic surfactant as a base, not containing an anionic one, being available in the commercial market, to prepare a detergent solution having a composition given in Table 3. Five black tea-stained cloths (8×8 cm$^2$) prepared by the above-mentioned procedure were washed with the detergent solution in a Terg-O-Tometer at 20° C. for 10 minutes, washed with water dried and examined for the rate of bleaching according to the above mentioned method.

Results are shown in Table 3, together with data of control compositions 7 to 10.

EXAMPLE 19

The three bleaching compositions, containing no phosphorus, a small amount of phosphorus and a considerable amount of phosphorus, respectively, were obtained in the below shown formulations. Percent is based on weight.

The composition containing no phosphorus was obtained from 14% of sodium linear dodecylbenzene sulfonate, 6% of polyoxyethylene (10 moles of EO) C12 to C13 alkyl ether, 2% of sodium salt of hardened beef tallow aliphatic acid, 5% of sodium silicate of 2 go, 10% of sodium carbonate, 25% of zeolite of the 4A type, 10% of sodium percarbonate, 10% of the cationic compound (IV-a), 2% of polyethylene glycol having a molecular weight of 6,000, 2% of protease, 4% of water and the balance of sodium sulfate.

The compound having a small amount of phosphorus was obtained from 10% of sodium linear dodecylbenzene sulfonate, 2% of sodium dodecylsulfate, 8% of polyoxyethylene (7.7 moles of EO) C12 to C13 alkyl ether, 2% of sodium salt of hardened beef tallow aliphatic acid, 5% of sodium silicate of 1 go, 10% of sodium carbonate, 20% of zeolite of the 4A type, 15% of sodium pyrophosphate, 10% of sodium perborate, 5% of the cationic compound (IV-a), 1% of polyethylene glycol having a molecular weight of 11,000, 1% of sodium sulfite, 2% of protease, 4% of water and the balance of sodium sulfate.

The compound containing a considerable amount of phosphorus was obtained from 20% of polyoxyethylene (8.6 moles of EO) beef tallow alcohol ether, 2% of sodium salt of hardened beef tallow aliphatic acid, 30% of sodium tripolyphosphate, 10% of sodium perborate, 5% of the cationic compound (IV-a), 5% of sodium silicate of 2 go, 10% of sodium carbonate, 1% of sodium sulfite, 2% of polyethylene glycol having a molecular weight of 6,000, 2% of protease, 6% of water and the balance of sodium sulfate.

TABLE 1

| | the invention | | | | | | | | control | | | |
|---|---|---|---|---|---|---|---|---|---|---|---|---|
| | 1 | 2 | 3 | 4 | 5 | 6 | 7 | 8 | 1 | 2 | 3 | 4 |
| composition (percent by weight) | | | | | | | | | | | | |
| sodium percarbonate | 93 | 89 | 90 | 88 | 92.5 | 92 | 93 | 90 | 88.5 | 94 | 87 | 100 |
| I-a | 7 | — | — | — | — | — | — | — | — | — | — | — |
| I-b | — | 11 | — | — | — | — | — | — | — | — | — | — |
| II-a | — | — | 10 | — | — | — | — | — | — | — | — | — |
| II-b | — | — | — | 12 | — | — | — | — | — | — | — | — |
| III-a | — | — | — | — | 7.5 | — | — | — | — | — | — | — |
| III-b | — | — | — | — | — | 8 | — | — | — | — | — | — |
| IV-a | — | — | — | — | — | — | 7 | — | — | — | — | — |
| IV-c | — | — | — | — | — | — | — | 10 | — | — | — | — |
| methyl-2-cyano-pyridinium iodide[1] | — | — | — | — | — | — | — | — | 11.5 | — | — | — |
| TAED[2] | — | — | — | — | — | — | — | — | — | 6 | — | — |
| magnesium mono-perphthalate[3] | — | — | — | — | — | — | — | — | — | — | 13 | — |
| bleaching extent (%)[4] | 37.0 | 35.7 | 37.3 | 41.6 | 40.0 | 38.7 | 47.3 | 44.1 | 13.2 | 20.3 | 21.4 | 18.3 (16.3) |

TABLE 2

| | the invention | | control | |
|---|---|---|---|---|
| | 9 | 10 | 5 | 6 |
| composition (percent by weight) | | | | |
| $H_2O_2$ | 0.106 | 0.106 | 0.106 | — |
| IV-a | 0.417 | — | — | — |
| IV-b | — | 0.505 | — | — |
| NaOCl | — | — | — | 0.063 |
| $Na_2CO_3$ | 0.333 | 0.333 | 0.333 | — |
| NaOH | — | — | — | 0.01 |
| concentration of available oxygen (%) | 0.05 | 0.05 | 0.05 | — |
| concentration of available chlorine (%) | — | — | — | 0.06 |
| bleaching extent | 77 | 73 | 21 | 63 |

TABLE 3

| | the invention | | | | | | | | control | | | |
|---|---|---|---|---|---|---|---|---|---|---|---|---|
| | 11 | 12 | 13 | 14 | 15 | 16 | 17 | 18 | 7 | 8 | 9 | 10 |
| detergent | 0.6 | 0.6 | 0.6 | 0.6 | 0.6 | 0.6 | 0.6 | 0.6 | 0.6 | 0.6 | 0.6 | 0.6 |
| sodium percarbonate | 0.013 | 0.013 | 0.013 | 0.013 | 0.013 | 0.013 | 0.013 | 0.013 | 0.013 | 0.013 | 0.013 | 0.013 |
| I-a | 0.013 | — | — | — | — | — | — | — | — | — | — | — |
| I-b | — | 0.013 | — | — | — | — | — | — | — | — | — | — |
| II-a | — | — | 0.013 | — | — | — | — | — | — | — | — | — |
| II-b | — | — | — | 0.013 | — | — | — | — | — | — | — | — |
| III-a | — | — | — | — | 0.013 | — | — | — | — | — | — | — |
| III-b | — | — | — | — | — | 0.013 | — | — | — | — | — | — |
| IV-a | — | — | — | — | — | — | 0.013 | — | — | — | — | — |
| IV-c | — | — | — | — | — | — | — | 0.013 | — | — | — | — |
| methyl-2-cyano-pyridinium iodide | — | — | — | — | — | — | — | — | 0.013 | — | — | — |
| TAED | — | — | — | — | — | — | — | — | — | 0.013 | — | — |
| magnesium mono-perphthalate | — | — | — | — | — | — | — | — | — | — | 0.013 | — |
| bleaching | 10.1 | 9.5 | 6.5 | 8.0 | 10.9 | 10.3 | 12.1 | 9.3 | 2.3 | 3.9 | 3.5 | 2.5 |

We claim:
1. A compound having the formula
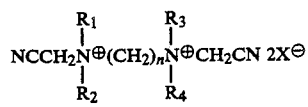
in which each of $R_1$, $R_2$, $R_3$ and $R_4$ is alkyl having 1 to 6 carbon atoms, n is an integer of 1 to 16 and X is an anion.
2. A compound as claimed in claim 1, in which in the formula each of R1, R2, R3 and R4 is an alkyl having 1 to 3 carbon atoms and n is an integer of 1 to 9.
3. A compound as claimed in claim 1, in which in the formula R1, R2, R3 and R4 are methyl and n is an integer of 1 to 9.
* * * * *